United States Patent [19]

Kurozumi et al.

[11] 4,001,308

[45] Jan. 4, 1977

[54] PROCESS FOR THE PREPARATION OF 1,4-DIACETOXYCYCLOPENT-2-ENE

[75] Inventors: Seizi Kurozumi; Takeshi Toru; Toshio Tanaka; Shuzi Miura; Makiko Kobayashi, all of Hino; Sachio Ishimoto, Tokyo, all of Japan

[73] Assignee: Teijin Limited, Osaka, Japan

[22] Filed: Dec. 13, 1974

[21] Appl. No.: 532,616

[30] Foreign Application Priority Data

Dec. 19, 1973   Japan .......................... 48-141180

[52] U.S. Cl. ................................................ 260/491
[51] Int. Cl.² ......................................... C07C 67/10
[58] Field of Search ........................... 260/491, 410

[56] References Cited

UNITED STATES PATENTS 2,296,823   9/1942   Pollock et al. ..................... 260/491
3,816,533   6/1974   Brandstrom et al. .............. 260/491

Primary Examiner—Vivian Garner
Attorney, Agent, or Firm—Sherman & Shalloway

[57] ABSTRACT

A process for the preparation of 1,4-diacetoxycyclopent-2-ene, which comprises contacting a solution of 1,4-dibromocyclopent-2-ene in an inert organic solvent which is slightly soluble or insoluble in water, with an aqueous solution or suspension of at least one metal salt of acetic acid which is at least partially water-soluble, in the presence of a cationic surface-active compound.

10 Claims, No Drawings

PROCESS FOR THE PREPARATION OF 1,4-DIACETOXYCYCLOPENT-2-ENE

This invention relates to a novel process for the preparation of 1,4-diacetoxycyclopent-2-ene. More particularly, the invention relates to a process for the preparation of 1,4-diacetoxycyclopent-2-ene from 1,4-dibromocyclopent-2-ene stereo-specifically and regio-specifically in high yield.

1,4-diacetoxycyclopent-2-ene is an extremely useful compound as an intermediate for synthesizing physiologically and biologically active substances including various medicines and agricultural chemicals. For instance, cis-1,4-diacetoxycyclopent-2-ene is extremely useful as the intermediate for making prostaglandin F-type compound which is very valuable as a medicine having a wide range physiological activity.

It is known to synthesize 1,4-diacetoxycyclopent-2-ene, for example, by treating 1,4-dibromocyclopent-2-ene (i) in acetic acid at 100° C. for 18 hours, together with potassium acetate; or (ii) in acetic acid at temperatures not higher than 30° C. for 16 hours, together with silver acetate; or (iii) in acetone at temperatures not higher than 0° C., for 16 hours, together with tetraethylammonium acetate. [See, L. N. Owen and P. N. Smith, J. Chem. Soc, (li52) 4035].

However, the above known method (i) fails to give 1,4-diacetoxycyclopent-2-ene selectively, but concurrently forms 3,4-diacetoxycyclopent-1-ene. The method (ii) is deficient in that it requires the use of costly silver acetate which is also unstable when exposed to light and heat, and furthermore does not give the object 1,4-diacetoxycyclopent-2-ene with satisfactory selectivity. While method (iii) does form 1,4-diacetoxycyclopent-2-ene selectively it consumes costly tetraethylammonium acetate in large quantities, and is industrially quite unsatisfactory because its yield of the object product is unduly low.

Accordingly, an object of the present invention is to provide a process for the preparation of 1,4-diacetoxycyclopent-2-ene which is useful as an intermediate of valuable medicines or pesticides, stereo- and regio-specifically in high yields.

Another object of the invention is to provide an industrial process for the preparation of 1,4-diacetoxycyclopent-2-ene.

Still many other objects and advantages of the invention will become apparent from reading the following descriptions.

According to the invention, the foregoing objects and advantages are accomplished by the process for the preparation of 1,4-diacetoxycyclopent-2-ene which comprises contacting a solution of 1,4-dibromocyclopent-2-ene in an inert organic solvent which is slightly soluble or insoluble in water, with an aqueous solution or suspension of at least partially water-soluble metal salt of acetic acid, in the presence of a cationic surface-active compound.

The process of the present invention includes the heterogeneous reaction of 1,4-dibromocyclopent-2-ene with a metal salt of acetic acid through the mediating action of a cationic surface-active compound in the heterogeneous reaction system composed of a solution of 1,4-dibromocyclopent-2-ene in an inert organic solvent which is slightly soluble or insoluble in water [the solution may be hereinafter referred to as the liquid (A)] and an aqueous solution or suspension of at least partially water-soluble metal salt of acetic acid [which may be hereinafter referred to as the liquid (B)], at the interface of the liquids (A) and (B).

The precise mechanism of the reaction of this invention is not yet clear, but the reaction of this invention is believed to proceed as follows. That is, at the interface of the liquids (A) and (B), first the salt of the cationic surface-active compound present therein and the metal salt of acetic acid present as dissociated in liquid (B) reach an equilibrium as below:

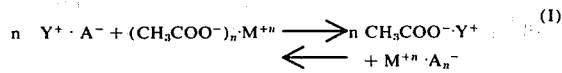

in which $Y^+$ denotes the cationic portion of the salt of cationic surface-active compound, $A^-$ denotes its counter anion, M denotes a metal atom, and $n$ denotes the valency of the metal atom.

Thus the cationic surface-active compound seizes acetate ions from the liquid (B), and then the acetate ions perform a substitution reaction with bromine in 1,4-dibromocyclopent-2-ene in the liquid (A), at the interface of the two phases, according to the reaction formula as below:

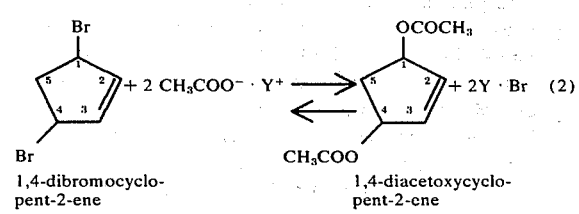

1,4-dibromocyclo-pent-2-ene     1,4-diacetoxycyclo-pent-2-ene thus giving 1,4-diacetoxycyclopent-2-ene, and simultaneously converting the cationic surface-active compound to a bromide. Thus the formed bromide of the cationic surface-active compound again seizes the acetate ions in the liquid (B) to participate in the reaction of the above formula (2).

Thus the reaction of the invention is believed to be an interfacial reaction between 1,4-dibromocyclopent-2-ene and a metal salt of acetic acid present each in the mutually different phase, with a salt of the cationic surface-active compound serving as an intermediary.

As the cationic surface-active compound useful for such interfacial reaction, any compound which is substantially insoluble both in the liquids (A) and (B), and which has a moiety having the surface activity to seize acetate ion from the liquid (B) at the interface of the two liquids (A) and (B), and to exchange the ion with the bromine atome of 1,4-dibromocyclopent-2-ene in the liquid (A), can be used.

As the compound having the cationic surface activity useful for the reaction of this invention, salts of nitrogen-containing or phosphorus-containing quaternary organic compounds, alkylamine salts, polyoxyalkylene-alkylamine, and the like are conveniently used. Examples of the typical cationic surface-active compound include the following:

1. Nitrogen-containing or phosphorus-containing quaternary organic compound of the formula,

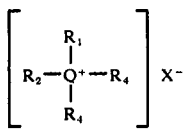

(I)

in which Q stands for nitrogen or phosphorus atom, $R_1$, $R_2$, $R_3$, and $R_4$ may be different or same, each denoting a hydrocarbon group, and $X^-$ stands for an anion.

In the formula above, the hydrocarbons which may be represented by $R_1$, $R_2$, $R_3$, and $R_4$ include alkyl, alkenyl, aryl, aralkyl, and cycloalkyl groups. Also the anion ($X^-$) can be, for example, halogen ions, particularly bromine or chlorine ions.

Specific examples of the salts of such quaternary organic compounds include the following: salts of nitrogen-containing quaternary compounds such as chlorinated or brominated tricaprylmethylammonium, chlorinated or brominated trioctylmethylammonium, chlorinated or brominated trioctylpropylammonium, chlorinated or brominated lauryltrimethylammonium, chlorinated or brominated stearyltrimethylammonium, chlorinated or brominated distearyldimethylammonium, chlorinated or brominated trimethyloctadecylammonium, chlorinated or brominated trimethyldodecylammonium, chlorinated or brominated trimethylhexadecylammonium, and the like; phosphorus-containing quaternary compounds such as brominated hexadecyltributylphosphonium, brominated lauryltributyl phosphonium, brominated decyltriphenylphosphonium, and the like.

2. Alkylamine salts such as laurylamine acetate, octadecylamine acetate, and the like.

3. Ammonium salts of polyoxyalkylenealkylamine of the formula,

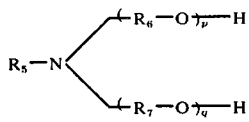

(II)

in which $R_5$ denotes an alkyl group, $R_6$ and $R_7$ each denotes an alkylene group which may be same or different, and $p$ and $q$ each denote an integer of no less than 1, for example, ammonium salt of polyoxyethylene alkylamine.

Of those cationic surface-active compounds, the salts of nitrogen-containing or phosphorus-containing quaternary organic compounds are preferred. Particularly, the salts of such nitrogen-containing quaternary organic compounds having at least 10 carbon atoms in total, i.e., referring to foregoing formula (I), the compounds of which $R_1$ through $R_4$ groups contain at least 10 carbon atoms in total, and preferably no more than 70, inter alia, 11–50 (quaternary ammonium salts) are the most preferred.

There is no critical limit to the amount of the cationic surface-active compound, which exhibits sufficient effect even when used in catalytic amount. Normally, however, it is used within the range of 0.01 to 1 mol, preferably 0.05–0.7 mol, inter alia, 0.1–0.5 mol, per mol of the 1,4-dibromocyclopent-2-ene employed.

As the solvent for dissolving 1,4-dibromocyclopent-2-ene to serve as the liquid (A), any inert organic solvent can be used so far as it is slightly soluble or insoluble in water and takes no part in the reaction. Preferred examples of such solvent include: aliphatic hydrocarbons such as pentane, hexane, petroleum ether, and cyclohexane; halogenated hydrocarbons such as carbon tetrachloride and dichloroethane; ethers such as ethyl ether; and aromatic hydrocarbons such as benzene, toluene, and xylene.

The concentration of 1,4-dibromocyclopent-2-ene in the solvent is not critical, but variable over a wide range depending on the types of the solvent and the cationic surface-active compound employed. Normally, however, the solvent is used within the range of 0.5–100 parts by weight, preferably 1–10 parts by weight, per part by weight of 1,4-dibromocyclopent-2-ene.

The metal for forming a metal salt of acetic acid in the liquid (B) again may be optionally selected, so far as the formed metal salt is at least partially soluble in water to dissociate acetate ions. As the metals usable for forming such metal salts, those of the Group Ia, Ib, IIa, IIb, VIIb, and VIII of the periodic table, such as lithium, sodium, potassium, copper, calcium, magnesium, barium, zinc, manganese, cobalt, lead, etc., can be named.

Of the above-named metals, alkali metals and alkaline earth metals are preferred, the optimum metals being lithium, sodium, potassium, magnesium, and barium.

When barium acetate is employed, the yield of 1,4-diacetoxycyclopent-2-ene is low compared with the case of using the acetate of lithium, sodium, potassium, or magnesium, but the embodiment is industrially advantageous because of the merit that when the resulting 1,4-diacetoxycyclopent-2-ene is subsequently hydrolyzed with barium hydroxide to be converted to 1,4-dihydroxycyclopent-2-ene, the side-produced barium acetate can be recycled into the reaction system composed of the liquids (A) and (B).

The above-named metal salts of active acid can be used either singly or in combination of two or more of different metal salts.

As the aqueous medium to form the solution or suspension of the metal salt or salts of acetic acid, water is the most preferred. It is permissible, however, for the water to contain a minor amount of water-miscible inert organic solvent, such as alcohol.

The metal salt of acetic acid is not necessarily substantially completely dissolved in the said aqueous medium, but only a part thereof is dissolved in the aqueous medium to dissociate acetate ions and the rest may be suspended in the medium without any detrimental effect.

The metal salt of acetic acid is used in at least equimolar amount to the starting 1,4-dibromocyclopent-2-ene, while there is no critical upper limit. Normally, however, the use of no more than 10 equivalent times is quite satisfactory, use of greater amount of the metal salt showing no justifying improvement in the result of the reaction. It is particularly convenient to use 1.5–5 equivalent times the starting 1,4-dibromocyclopent-2-ene of the metal salt.

According to the present invention, a solution of 1,4-dibromocyclopent-2-ene in an inert organic solvent which is slightly soluble or insoluble in water [liquid (A)] and an aqueous solution or suspension of a metal salt or salts of acetic acid which is at least partially water-soluble [liquid (B)] are contacted in the presence of a cationic surface-active compound as described above.

Because the reaction in accordance with the invention is a heterogeneous reaction at the interface of the liquids (A) and (B) as aforesaid, it is desirable that the contact of the two liquids should be as intimate as possible.

Satisfactorily intimate contact of the liquids (A) and (B) can be accomplished, for example, by violent agitation of a mixture of the two liquids. For instance, first the liquids (A) and (B) are mixed, and to the mixture a cationic surface-active compound is added and violently stirred; or initially the cationic surface-active compound and metal salt or salts of acetic acid are dissolved or dispersed in an aqueous medium, to which 1,4-dibromocyclopent-2-ene solution in an inert organic solvent is slowly added under violent stirring.

The mixing ratio of the liquid (A) and liquid (B) is not critical, but they can be mixed at an optional ratio.

The contact of the liquids (A) and (B) can be normally effected at the temperatures ranging from 0° to 150° C., preferably not lower than 20° C., more preferably from 30° to 60° C. While atmospheric pressure is quite sufficient for the reaction, reduced or elevated pressure may be employed if necessary.

The progress of the reaction can be decided by tracing the consumption of the starting 1,4-dibromocyclopent-2-ene by such analytical means as thin layer chromatography, gas chromatography, and the like.

The reaction time differs depending on such factors as the reaction temperature, mixing ratio of the liquids (A) and (B), manner of agitation, etc., but normally that of 5 to 10 hours is employed.

It is desirable to effect the reaction in an atmosphere of an inert gas, such as argon or nitrogen, in order to prevent undesirable side reactions such as oxidation of the starting material and the reaction product.

After completion of the reaction, 1,4-diacetoxycyclopent-2-ene can be separated from the reaction mixture and refined by means known per se, for example, extraction, distillation, thin layer chromatography, gas chromatography, or the like.

As so far described in detail, according to the invention, 1,4-diacetoxycyclopent-2-ene which is extremely useful as an intermediate for synthesizing biologically active compounds such as medicines and pesticides, can be advantageously formed without using rare or costly starting material, but from 1,4-dibromocyclopent-2-ene, through simple operations in high yields. Thus the process of the invention achieves conspicuous industrial effect.

The subject process also is characterized in that the reaction progresses stereo- and regio-specifically. Accordingly, the process has such an advantage that, when cis-1,4-dibromocyclopent-2-ene, for example, is used as the starting material, cis-1,4-diacetoxycyclopent-2-ene can be formed with high selectivity.

The invention will be hereinafter more specifically explained with reference to the working Examples, it being clearly understood that the scope of this invention is in no way limited thereby.

EXAMPLE 1

Three (3.0) g of potassium acetate and 0.7 g of trioctylpropylammonium chloride were dissolved in 20 ml of water, and to the solution 2.0 g of cis-1,4-dibromocyclopent-2-ene as dissolved in 5 ml of carbon tetrachloride was added. The system was allowed to react at 42° C. for 9 hours, under violent agitation by a stirring motor, in the atmosphere of nitrogen. Then 50 ml of ether and 10 ml of water were added to the system, and the organic phase was separated. The aqueous phase was extracted once with 20 ml of ether. The resulting organic phases were combined, washed with 10 ml of water, and then dried over sodium sulfate. The solvent was distilled off with a rotary evaporator, and the residual oily substance was subjected to a reduced pressure distillation. Thus 1.33 g of a reaction product (yield 75%) boiling at 76°–77° C./0.1 mmHg was obtained, which was identified to be cis-1,4-diacetoxycyclopent-2-ene because its gas chromatogram, thin layer chromatogram, nuclear magnetic resonance absorption spectrum, infrared spectrum and mass spectrum coincided with those of cis-1,4-diacetoxycyclopent-2-ene separately synthesized from cis-1,4-dibromocyclopent-2-ene and tetraethylammonium acetate [J. Chem. Soc. 4042 (1952)].

EXAMPLE 2

One (1.0) g of cis-1,4-dibromocyclopent-2-ene, 3.5 g of potassium acetate, 0.7 g of cetyltrimethylammonium chloride, 5 ml of carbon tetrachloride, and 2 ml of water were used in the manner similar to the Example 1, at 42° C. for 6 hours. After addition of 30 ml of ether, the organic phase was dried over sodium sulfate, and the organic solvent was distilled off under a reduced pressure similarly to Example 1. Further subjecting the residual system to a reduced pressure distillation, 0.7 g of cis-1,4-diacetoxycyclopent-2-ene boiling at 60°–61° C./0.03 mmHg was obtained. The yield was 77%.

EXAMPLE 3

Three (3.0) g of potassium acetate and 0.7 g of trioctylpropylammonium chloride were dissolved in 2 ml of water, and while stirring violently in nitrogen atmosphere at 60° C., 2.0 g of 1,4-dibromocyclopent-2-ene as dissolved in 5ml of benzene was added thereto, consuming 2.5 hours. The stirring was continued for additional 2.5 hours, and then the reaction mixture was treated similarly to Example 1. Upon the final reduced pressure distillation, 1.20 g of cis-1,4-diacetoxycyclopent-2-ene boiling at 69°–70° C./0.07 mmHg was obtained. The yield was 68%.

EXAMPLES 4 THROUGH 14.

The metal salts of acetic acid as shown in the table below and trioctylpropylammonium chloride were dissolved in water, and to the solution was added 1,4-dibromocyclopent-2-ene dissolved in carbon tetrachloride. The system was then allowed to react at the temperature and for the time both indicated in the same table, in the atmosphere of nitrogen under violent agitation by a stirring motor. After completion of the reaction, the reaction mixture was treated similarly to Example 1. The yield of 1,4-diacetoxycyclopent-2-ene was analyzed by gas chromatography. The results are also shown in the table below.

| Ex. No. | Metal salt of Acetic acid g(mmol) | Trioctyl-propylammonium chloride mg(mmol) | 1,4-Dibromo-cyclopent-2-ene g(mmol) | Solvent water (ml) | Solvent Carbon Tetra-chloride (ml) | Temp. (° C.) | Time (hr) | Yield (g) | Yield of 1,4-Diacetoxy-cyclopent-2-ene g(mmol) | Yield (%) |
|---|---|---|---|---|---|---|---|---|---|---|
| 4 | LiOAc.2H₂O 10.2(100) | 860(2) | 2.26(10) | 6 | 15 | 70 | 5 | 2.73 | 0.96(5.2) | 52 |
| 5 | NaOAc.3H₂O 4.08(30) | " | " | 2 | 6 | 60 | 4 | 1.91 | 0.69(3.7) | 37 |
| 6 | KOAc 2.94(30) | *1,140(5) | " | 4 | 10 | 60 | 18 | 1.25 | 0.25(1.4) | 14 |
| 7 | Cu(OAc)₂.H₂O 6.0(30) | 8860(2) | " | 6 | 15 | 60 | 3 | 1.35 | 0.27(1.5) | 15 |
| 8 | Ca(OAc)₂ 2.64(15) | " | " | 3.5 | 6 | 55 | 4 | 1.71 | 0.15(0.8) | 8 |
| 9 | Zn(OAc)₂.2H₂O 6.6(30) | " | " | 10 | 25 | 60 | 3 | 0.78 | 0.24(1.3) | 13 |
| 10 | Mn(OAc)₂.4H₂O 7.35(30) | " | " | 10 | 25 | 70 | 5 | 2.82 | 0.31(1.7) | 17 |
| 11 | Co(OAc)₂.4H₂O 7.5(30) | " | " | 10 | 25 | 70 | 3 | 2.26 | 0.27(1.5) | 15 |
| 12 | Pb(OAc)₂.3H₂O 11.4(30) | " | " | 3 | 7 | 60 | 6 | 0.92 | 0.16(0.9) | 9 |
| 13 | Ba(OAc)₂ 7.65(30) | " | " | 4 | 7 | 60 | 6 | 1.2 | 0.25(1.4) | 14 |
| 14 | Mg(OAc)₂.4H₂O 6.42(30) | " | " | 4 | 8 | 60 | 6 | 0.8 | 0.63(3.5) | 35 |

In the table, *mark denotes that triethylbenzylammonium chloride was used in place of trioctylpropylammonium chloride.

We claim:

1. A process for the preparation of 1,4-diacetoxycyclopent-2-ene, which comprises contacting a solution (A) of 1,4-dibromocyclopent-2-ene in an inert organic solvent which is slightly soluble or insoluble in water, with an aqueous solution or suspension (B) of at least one metal salt of acetic acid which is at least partially water soluble, in the presence of a cationic surface active compound which is substantially insoluble both in the solution (A) and the aqueous solution or suspension (B), and is selected from the group consisting of
  1. nitrogen-containing or phosphorus-containing quaternary organic compounds of the formula:

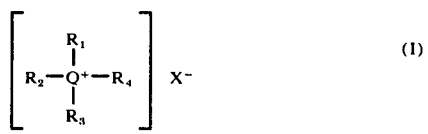

in which Q stands for nitrogen or phosphorus atom, R₁, R₂, R₃, and R₄ may be different or same, each denoting a hydrocarbon group, and X⁻ stands for a halogen ion, and
  2. alkylamine salts selected from the group consisting of laurylamine acetate and octadecylamine acetate.

2. The process according to claim 1 in which the cationic surface-active compound is said salt of a nitrogen- or phosphorus-containing quaternary organic compound of formula (1).

3. The process according to claim 1, in which the cationic surface-active compound is said salt of a nitrogen-containing quaternary organic compound of formula (1) containing at least ten carbon atoms in total.

4. The process according to claim 1, in which the cationic surface-active compound is present in the system at a ratio of 0.01–1 mol per mol of 1,4-dibromocyclopent-2-ene.

5. The process according to claim 1, in which the metal salt of acetic acid is an alkali metal salt or alkaline earth metal salt of acetic acid.

6. The process according to claim 1, in which the metal salt of acetic acid is the acetate of at least one metal selected from the group consisting of lithium, sodium, potassium, magnesium and barium.

7. The process according to claim 1, in which the metal salt of acetic acid is used in the amount at least equivalent, but not more than 10 equivalents, to 1,4-dibromocyclopent-2-ene.

8. The process according to claim 1 which comprises contacting solution (A) with the aqueous solution or suspension (B) at a temperature between 0° and 150° C.

9. The process according to claim 1 in which the cationic surface-active compound is a nitrogen-containing quaternary compound selected from the group consisting of chlorinated or brominated tricaprylmethylammonium, chlorinated or brominated trioctylpropylammonium, chlorinated or brominated lauryltrimethylammonium, chlorinated or brominated stearyltrimethylammonium, chlorinated or brominated distearyldimethylammonium, chlorinated or brominated trimethyloctadecylammonium, chlorinated or brominated trimethyldodecylammonium, and chlorinated or brominated trimethylhexadecylammonium.

10. The process of claim 1 in which the cationic surface-active compound is a phosphorus-containing quaternary compound selected from the group consisting of brominated hexadecyltributylphosphonium, brominated lauryltributyl phosphonium and brominated decyltriphenylphosphonium.

* * * * *